(12) United States Patent
Magagnoli (10) Patent No.: US 11,925,560 B2
(45) Date of Patent: Mar. 12, 2024

(54) DEVICE IMPLANTABLE IN A HUMAN BODY AND PRODUCTION METHOD THEREOF

(71) Applicant: COSSINGTON LIMITED, Kingston upon Thames (GB)

(72) Inventor: Augusto Magagnoli, Cervia (IT)

( * ) Notice: Subject to any disclaimer, the term of this patent is extended or adjusted under 35 U.S.C. 154(b) by 6 days.

(21) Appl. No.: 16/850,246

(22) Filed: Apr. 16, 2020

(65) Prior Publication Data

US 2020/0315804 A1 Oct. 8, 2020

Related U.S. Application Data

(63) Continuation-in-part of application No. 14/701,398, filed on Apr. 30, 2015, now Pat. No. 10,993,810.

(30) Foreign Application Priority Data

Feb. 16, 2015 (IT) .................................. 2015000065

(51) Int. Cl.
*A61F 2/30* (2006.01)
*A61F 2/38* (2006.01)

(52) U.S. Cl.
CPC ........ *A61F 2/30724* (2013.01); *A61F 2/3859* (2013.01); *A61F 2002/30677* (2013.01); *A61F 2002/30726* (2013.01)

(58) Field of Classification Search
CPC ................ A61F 2/30724; A61F 2/3859; A61F 2002/30726; A61F 2002/30677
See application file for complete search history.

(56) References Cited

U.S. PATENT DOCUMENTS

| | | | | |
|---|---|---|---|---|
| 5,984,968 A * | 11/1999 | Park | ................... | A61B 17/8802 623/16.11 |
| 6,953,594 B2 * | 10/2005 | Lee | ......................... | A61L 27/12 424/422 |
| 10,206,783 B2 * | 2/2019 | Magagnoli | .............. | A61F 2/389 |
| 2006/0178749 A1 * | 8/2006 | Pendleton | ................. | A61F 2/38 623/20.15 |
| 2009/0222103 A1 * | 9/2009 | Fitz | ....................... | A61F 2/3872 623/18.11 |
| 2011/0060373 A1 * | 3/2011 | Russell | .............. | A61B 17/8057 606/304 |

* cited by examiner

*Primary Examiner* — Dinah Baria
(74) *Attorney, Agent, or Firm* — Themis Law (57) ABSTRACT

A device implantable in a human body comprising a first component, or main support component, delimiting a plurality of openings, and a second component disposed on a surface of the main support component.

16 Claims, 4 Drawing Sheets

DEVICE IMPLANTABLE IN A HUMAN BODY AND PRODUCTION METHOD THEREOF

FIELD OF THE INVENTION

The present invention refers to a device implantable in the human body, such as a joint space, a prosthesis or also another kind of device, such as a cranial operculum or cranial prosthesis or vertebra or bone part for completing a bone portion which has been surgically removed, added with a thermally sensitive pharmaceutical active ingredient. The present invention refers also to a method for obtaining such device.

BACKGROUND OF THE INVENTION

More and more often the need is felt of providing devices and generally aids to be implanted in the human body that are customized or tailored for the patient to be treated, this for improving the effectiveness of the implant and the safety for patients' health.

A number of companies already produce customized prostheses and other aids for hospitals.

However, such solutions are not fully satisfactory, as they are difficult to implement and therefore very often expensive.

Cheaper solutions do not usually have the desired characteristics.

Moreover, a problem also arises from the fact that these products must receive the necessary authorization from the competent bodies, which naturally makes it much more difficult to put them on the market.

It is also noted that what is now indicated applies in particular to the field of prostheses and joint spacers.

With regard to spacers, it is known that prostheses implanted inside the human body may be prone to infections and, in this case, the infected prosthesis must be removed from the implantation site and, before the implantation of a new prosthesis, the infection must be eradicated.

During this phase, spacer devices are normally used to maintain substantially unchanged the shape of the bone seat or of the joint seat where the new prosthesis will be implanted.

This procedure is known as "two-step treatment" for the removal of an infected prosthesis and the implantation of a new prosthesis.

SUMMARY OF THE INVENTION

The purpose of the present invention is to provide a new implantable device.

An additional purpose of the present invention is to provide a device as mentioned above that is simple and easy to obtain.

Another purpose of the present invention is to provide a temporary and/or disposable spacer device for the essentially uniform release of at least one pharmaceutical or medical substance in a bone or joint area to be treated.

An additional purpose of the present invention is to provide a device as indicated above that it is resistant.

Another purpose of the present invention is to provide a device that can be implanted in the human body that is customized or substantially tailor-made on a patient.

Another purpose of the present invention is to provide a customized implantable device that allows obtaining the necessary authorizations for commercial release in an easy way.

In accordance with one aspect of the present invention, an implantable device is provided according to claim 1.

In accordance with another aspect of the present invention, a spacer device for the treatment of a bone or joint seat is provided according to claims 16, 21, 22 and 23.

Such a spacer device is provided for the release of a pharmaceutical or medical substance evenly substantially across the entire outer surface of the spacer device itself.

In addition, such a spacer device can be made so that the release of such a pharmaceutical or medical substance is guaranteed even for long periods.

In accordance with an additional aspect of the present invention, a method for obtaining an implantable device, for example for the treatment of a bone or joint seat, is provided according to claim 24.

The dependent claims refer to preferred and advantageous embodiments of invention.

BRIEF DESCRIPTION OF THE DRAWINGS

Further characteristics and advantages of the present invention will become clearer from the detailed description of preferred but not exclusive embodiments of implantable devices, illustrated for indicating but not limiting purposes in the attached tables of drawings, in which:

In FIGS. 9a and 9b, the main component is shown in cross-section and the holes in the main component are depicted enlarged for ease of representation.

DETAILED DESCRIPTION OF EMBODIMENTS OF THE INVENTION

With reference first to FIGS. 1 to 6, it is showed a device 1 implantable in the human body, such as a temporary and disposable joint spacer device, such as a knee, elbow, shoulder, hip spacer device or a component for the same, a prosthesis or a respective component, for example a cranial prosthesis or a rib prosthesis or a portion of the pelvis replacing an original bone surgically removed because it was pathological, or a reconstruction of a pathological vertebra surgically removed.

In general, a device according to the present invention can be used to replace any part of bones surgically removed. To such a device, as will be better explained below, a thermally sensitive pharmaceutical active ingredient is advantageously added.

Such a device comprises a first component or main support component 2 delimiting a plurality of holes 3, through-holes or not, and at least a second component 4 applied on at least one surface 2a, 2b of the main support component 2.

The second component 4 comprises a dough 5 applied and hardened or solidified on a surface 2a, 2b and at least partly within holes 3, preferably also through the holes 3, which dough includes a matrix of at least one first compound and at least one pharmaceutical or medical substance dispersed in the matrix.

Preferably, the second component 4 is a component that stiffens or increase the resistance of the main component 2.

In addition to this, the second component 4 and, more particularly the first compound thereof, can be intended to convey, in use, the pharmaceutical or medical substance from the device 1 to the outside thereof and in the implant site, if in particular the main component 2 is not able to carry out such function. Clearly, with the word "convey" it is meant that the second component is able to release the pharmaceutical or medical substance in the implant site.

According to one variant, the second component 4 is provided only to convey the pharmaceutical or medical substance, while it does not perform any function of stiffening of the main component 2 or otherwise the effect of such stiffening or increase of resistance is negligible.

Of course, if the holes 3 are through-holes from a first 2a to a second 2b surface of the main component 2, the application of the dough on a surface 2a can lead to the spill or reaching by the dough also on or to another surface 2b of the main component 2.

Advantageously, the holes 3 have a passage section for example of 0.05 to 10 mm, if desired of 0.1 to 5 mm, preferably of 2-3 mm or 4-5 mm. If desired, the holes are at a distance from each other of 0.1 to 5 mm.

Preferably, the holes 3 are distributed on an area that is at least 50% or 60% or 70% or 80% or 90% of the main component 2.

With reference instead to the main support component 2, it can have a thickness for example of 0.1 to 100 mm, if desired of 0.5 to 50 mm, preferably 2-5 mm or 10-30 mm or 40-50 mm.

The main component 2 may or may not have constant thickness.

Clearly, the main component could be in one piece or even include multiple elements that are properly constrained to each other, for example with bone cement.

Such thickness can be chosen according to specific use requirements such as the conformation of the spacer device that is intended to be obtained or the structural strength that it must guarantee.

The viscosity or pastiness of the dough can be between 1000 and 100,000 centipoises.

The second component can have a thickness for example between 0.1 mm and 100 mm, if desired between 0.5 mm and 50 mm, preferably 2-3 mm or 4-5 mm.

The main component 2 can also include a plurality of reference elements 7 to define the area of application of the dough on a first surface 2a, preferably concave or with a raised edge. These reference elements may include pegs or projections 7 extending, from each other spaced, from a first surface 2a of the main component 2; the pegs or projections 7 have therefore a distal free end from the respective surface 2a.

If desired, the pegs or projections 7 are parallel or inclined relative to each other of an angle between 0 and 30 degrees or in any case they extend from a first surface 2a away from it.

The pegs are very thin or in any way they can have a section between 1 and 10 mm, if desired between 1 and 5 mm.

Moreover, pegs or projections 7, if provided are distributed on a first surface 2a, so that the area defined by the perimeter or line passing through the pegs or projections 7 outermost or closest to the periphery of the first surface 2a is at least 60% or 70% or 80% or 90% of the latter. Clearly, the pegs or projections 7 are distributed evenly or otherwise present in several parts of the respective surface of the 2a.

The pegs or projections 7 can have a height between 1 and 10 mm, for example 7-9 mm, preferably 8 mm.

Advantageously, the main support component 2 includes at least two main opposite external or more external surfaces 2a, 2b, a first surface 2a and a second surface 2b, while the second component 4, if desired to stiffen, is applied on one or preferably both surfaces 2a, 2b. Clearly, if the second component is applied, if desired to stiffen, on an external surface of the main component 2, this surface is no more (in whole or in part) exposed.

Even more advantageously, the second component 4 completely covers the main support component 2.

Preferably, the device 1 does not comprise any closure component, but it consists only of the main support component 2 and of the second component 4 which constitute an implantable assembly as it is, and without the need for other elements, in the human body. More specifically, there are no closing components which define together with the main component a positioning zone of the stiffening component.

In essence, the main component 2 and the second component 4 define all the external surfaces of the device 1, i.e. the surfaces of the same that will come or are destined to come into contact with respective parts of the human body, such as bones, biological fluids, skin, etc.

With regard to this aspect, the second component 4 defines one or more work surfaces 4a, in use, external or intended to be external in use or during implantation in the human body of the device 1.

This/these external work surface/surfaces 4a will therefore complete the exterior of the device together with other surfaces 2b, 2e defined by the main component 2.

In the event that the second component 4a covers all the surfaces of the main component 2 then it will define all the surfaces of the device towards the outside of the same.

With regard to what is now indicated, the second component 4 is advantageously applied so as to protrude with respect to a respective application surface or in any case to protrude with respect to or be flush or in line and not in recess with the end of a delimiting edge of an application area of the second component 4.

If desired, the main support component 2 or rather a respective first surface 2a delimits a concave area CZ, with concavity facing away from component 2, which concave area is for housing the second component 4. In such case, the concave area CZ presents a height between 5 and 200 mm, if desired between 10 and 100 mm.

In this case, the second component 4 is applied so as to protrude with respect to or be flush or in line and not in recess with the end of a delimitation edge of the concave area CZ.

If two surfaces 2a, 2b as indicated above are provided, then the second surface 2b can be a convex surface, with convexity facing away from the main component 2.

By "concave" in the present description it is meant a regular or irregular shaped surface such as to define a recess basin defined by or in the main component 2.

By "convex" in the present description it is meant instead a surface of regular or irregular shape such as to define a protruding part defined by the main component 2.

Preferably, the main support component 2 has substantially the final shape of the device, with the concave area CZ and/or the convex surface 2b coated, in whole or in part, with the second component 4, if desired to stiffen.

A device according to the present invention can comprise an articular spacer or a prosthesis.

Advantageously, the main component 2 is made of a biologically compatible material.

According to a version of the present invention, the main component 2 is made of a porous material.

So for example, such biologically compatible material can be selected among plastic and/or polymeric materials, such as polymethylmethacrylate (PMMA), polyethylene (PE), polyvinylchloride (PVC), polystyrene (PS), polyether ether ketone (PEEK), ultra-high molecular weight polyethylene (UHMWPE), high or low density polyethylene, or non-polymeric materials, ceramics, metals, metal alloys, organometallic compounds, and/or a combination thereof.

With reference to the biocompatible plastic materials, sufficiently rigid ones at a temperature of about 36° C., i.e. the physiological temperature, are preferable, at the same time guaranteeing the necessary mechanical performances according to the present invention and described in the present specification.

Specifically, the aforementioned plastic materials can be chosen among thermoplastic polymers, such as acrylic resins, polyethylene, polypropylene, polyester, etc., thermoformable polymers, and other similar materials.

In a version of the present invention, the biologically compatible material is a polymethylmethacrylate (PMMA) based bone cement. PMMA has the advantage of being perfectly welded with the material of the second component which, at least in one version of the invention, is bone cement which also includes PMMA being polymerized.

Preferably, the aforementioned biologically compatible material is free of pharmaceutical or medical substances.

Preferably, the first compound is made of a bone cement.

The first compound may alternatively include an inorganic hydraulic cement or a biocompatible solid filler material.

According to a further version of the present invention, the first compound can be a ceramic cement, such as for example the calcium sulphate known as gypsum or $CaSO_4$, which in addition to solidifying in a short time is able to release calcium ions.

According to another version, the first compound could be based on complex ceramic cements based on Silicates and Calcium Aluminates.

According to a further version, the first compound can be a liquid or a fluid whose viscosity is chosen according to the duration of the period necessary for the treatment of the infected site, as better described hereinafter.

Thus, for example, the liquid or fluid of the first compound could be able to be eluted through the main component 2 for a period of time ranging from 1 to 12 months.

However, further first compounds of biocompatible kind can be used, with respect to the above, without thereby departing from the scope of protection of the present right.

The first compound can be added with the medical and pharmaceutical substance by the surgeon or it can already be provided with this substance.

Once hardened, the first compound can be porous.

The pharmaceutical or medical substance is chosen from the group consisting of at least one antibiotic, such as aminoglycosides, such as gentamicin or vancomycin, or any other of the medical formulary at the discretion of the surgeon with proven compatibility with the first compound.

The amount of pharmaceutical or medical substance in the first compound varies according to the potency of the substance and the therapeutic modalities that the doctor in collaboration with the pharmacologist decide to adopt.

As a safety limit, the quantity of drug inserted into an implantable medical device corresponds to the maximum daily dose per kilogram of patient. This caution is adopted in particular if the first compound, once hardened, has high porosity, since in this case the substance comes out abundant and toxic levels are not wanted to be reached. This dose can also be increased up to ten times the maximum daily dose if the first compound, once hardened, is not very porous. So, for example, bone cement releases a very small amount of a drug.

Taking into account what has now been indicated, the quantity of pharmaceutical or medical substance in the first compound can vary between 0.5 and 100 times the maximum daily dose per kilogram of patient.

A device according to the present invention could also contain metal reinforcements which would be integrally cemented so as to release antibiotic or pharmaceutical or medical substance.

The device 1 is designed to be implanted in a bone or joint seat of the human body, for example in replacement of an infected prosthesis.

If the device 1 comprises a spacer device, the latter is "temporary" in the sense that, once it has performed its healing function and of maintaining the space of the bone or joint seat, it will be removed from the area in question and replaced for example with a permanent prosthesis.

In this regard, a spacer device performs a function of maintaining joint spaces as well as of treating bone infection by releasing a quantity of antibiotic or a pharmaceutical or medical substance in the infected area. Regarding this aspect, a spacer can cure an ongoing infection by releasing a pharmacological substance, such as an antibiotic, in a targeted manner and in infinitesimal quantities, while the application of even high doses of antibiotic, but with methods that do not provide for the use of spacers, such as washing the infected place with high dosage antibiotic solutions, does not allow obtaining the same results.

In the case of the use of a joint spacer it is essential that it extends over the whole area of the infection, so if a long infected prosthesis is to be replaced, a long spacer will be used and in case the infected prosthesis is of short type, a short spacer will be used.

In general, the device 1, be it a spacer, a prosthesis or other type of implantable device, such as a cranial prosthesis, has a shape such as to be coupled, in a substantially complementary way, to the bone or joint seat to which it must be constrained.

Such a temporary and/or disposable spacer device, once formed, therefore comprises a main component 2 completely or in part covered with the second component 4 suitably hardened or solidified.

A device 1 according to the present invention, if it includes a joint spacer, could include for example:
  a tibial component of a temporary and disposable knee joint spacer device, i.e. a component that can be constrained to a patient's tibia,
  a femoral component of a temporary and disposable knee joint spacer device, i.e. a component that can be constrained to a patient's femur,
  a temporary and disposable spacer device for the shoulder or hip joint.

As indicated above, a device according to the present invention can be any device necessary to replace or complete a bone deficiency following surgical removal in order to at least partially restore the bone function otherwise compromised by a resection.

Clearly, further configurations of the device according to the present invention are possible, for the realization of spacer devices shaped in a different way with respect to what is illustrated in the attached figures without any limitation.

With particular reference to the through or not holes 3, they are preferably homogeneously distributed throughout the entire volume of the main component 2 or at least in the volume of a part thereof.

The holes 3, if passing through, for example, can put in fluid communication a first surface 2a of the main component with a second surface 2b and therefore, in use, the area on one side of the device 1 and the area on an opposite side.

Therefore, in the event that the pharmaceutical or medical substance is placed or applied or spread on a surface 2a of the main component, the holes 3, whether passing through or not, favor its release also through the main component 2 itself.

The size of the holes 3 can be such as to prevent, in use, bone regrowth inside the main component 2 and, therefore, inside the device 1, in particular if the latter includes a temporary and/or disposable spacer.

In this case, the configuration of the holes 3 facilitates the subsequent removal of the spacer device from the treated bone or joint seat, once its curative function has been carried out.

In the event that the device is not a spacer device, this may not be necessary.

The holes 3 can have a circular cross section or with any other geometry suitable for the purpose. Of course, the cross section of the holes 3 may also not be constant along the development of the holes 3 themselves.

As for the specific configuration of the main component 2, if the respective device is a cranial prosthesis, it could have a concave configuration or with a flat or slightly curved main plate or wall 2c, if desired with a perimeter edge 2d extending from the periphery of the same so as to define a concave area CZ.

According to this variant, the pegs or projections 7 have a free end substantially in the same plane in which the terminal end of the perimeter edge 2d lies.

In this case, the first 2a and the second 2b surface would constitute the opposite main surfaces of the flat or slightly curved main wall 2c.

According to this variant, the second component 4 could be applied on the first surface 2a and/or on the second surface 2b as well as on the outer edge surface 2e, i.e. the outer surface of the perimeter edge 2d.

This may also apply in general to other types of prostheses or spacers or implantable devices in general.

Advantageously, the second component 4 is applied so as to protrude with respect to or be flush or in line and not in recess with the end of the perimeter edge 2d.

For example, if the device is a tibial component (see FIG. 7) then a respective main component 20 of a tibial component of a temporary and disposable knee joint spacer device, i.e. a component that can be constrained to a patient's tibia, then such component could include a base portion with a first tibial joint surface 20a facing or destined to be turned in use or following implantation towards a traditional femoral component or as indicated below 30 and a second tibial connection surface 20b, if desired substantially flat, opposite the first surface 20a.

In this case, the main component 20 of a tibial component could also include a first stem (not shown in the figures), if desired removable, for example connectable by screwing to the base portion, which rises from the second tibial connection surface 20b of the base portion and is intended to be grafted into a patient's tibia.

The first stem extends, in use, in a substantially longitudinal direction with respect to the patient's tibial bone in which it is to be implanted.

Figure 7:
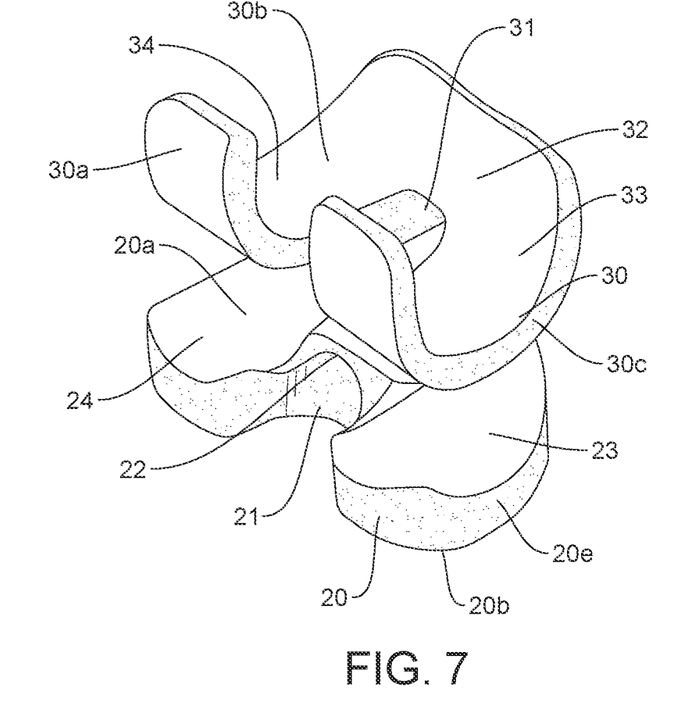
FIGS. 7 and 8 show respective main components for a device according to the present invention.

If desired, the base portion of the main component 20 of a tibial component is substantially C-shaped and delimits a first channel 21 passing through and extending from the first surface 20a to the second connection surface 20b.

The first joint surface 20a can have a raised intermediate part 22, as well as two lowered lateral parts 23, 24 placed one opposite the other with respect to the intermediate part 22. For this purpose, the main component 20 of a tibial component can be equipped with an intermediate section with a greater thickness, as well as two lateral sections with a lesser thickness placed one opposite the other with respect to the intermediate section.

The raised intermediate part 22 extends longitudinally to the sagittal plane of the knee.

In this case, the second component 4 (not visible in FIG. 7) could be applied on the first surface 20a and/or on the second surface 20b as well as on the outer edge surface 20e.

Of course, if the second component 4 is applied on the first surface 20a, it defines the joint surface which, in use, will engage by roto-translation a respective joint surface of a femoral component 30. In this case, the expression first joint surface 20a would mean that this first surface is the one underlying that of actual articulation defined by the second component 4.

If in alternative or in addition to that the second component 4 is applied on the second surface 20b, it defines the connection surface which, in use, will engage or come into contact with the tibia.

Figure 10:
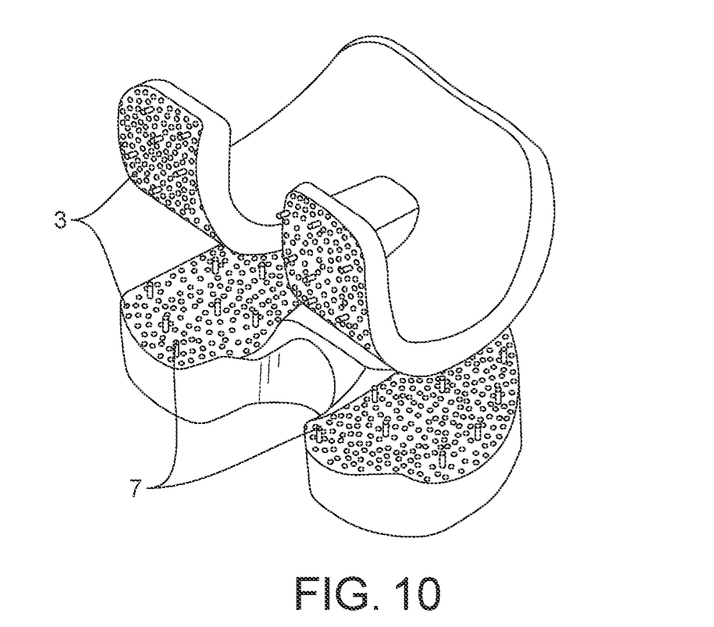
FIGS. 10 and 11 show an embodiment of the invention, in which the main support component is configured as a joint having femoral and tibial portions, with the opposing connection surfaces of the femoral and tibial portions having a plurality of reference elements (FIG. 10) and being covered with the second component (FIG. 11).

In this regard, the main component 20 has holes 3, whether through or not, and pegs 7, as shown in FIG. 10.

With regard to this, the holes 3 could either extend from the first 20a to the second 20b surface or be blind holes on one or both of these faces.

Preferably, in this case the holes 3 could be formed in a substantially uniform manner and as indicated above on the first surface 20a.

Clearly, a tibial component could be in one piece or even include several elements suitably constrained to each other, for example with bone cement.

If instead the device is a femoral component of a temporary and disposable knee joint spacer device then the main component 30 (see FIG. 7) of a femoral component can delimit a first femoral joint surface 30a facing or intended to be facing in use or following the implant towards a traditional tibial component or as previously indicated 20 and a second tibial connection surface 30b opposite the first surface 30a.

If desired, this main component 30 of a femoral component further comprises a second stem (not shown in the figures), if desired also removable, for example connectable by screwing, which rises from the second surface 30b and is intended to be inserted in the femur of a patient.

The main component 30 of a femoral component can furthermore be substantially C-shaped and delimit a second channel 31 extending from the first surface 30a to the second surface 30b.

In use, the second channel 31 and the first channel 21 are substantially aligned or one after the other, so as to define a main rear opening of the device.

Moreover, the main component 30 of a femoral component comprises a substantially curved plate-like body with a convexity facing the tibial component 20.

The first tibial joint surface 30a can have a central hollow band 32, in use intended to engage in a slide way the raised intermediate part 22 of the tibial component, as well as two enlarged lateral bands 33, 34 placed one opposite to the other with respect to the hollow band 32 and each destined to slidingly engage a respective lowered lateral part 23, 24. The central hollow band 32 extends longitudinally to the sagittal plane of the knee.

Figure 11:
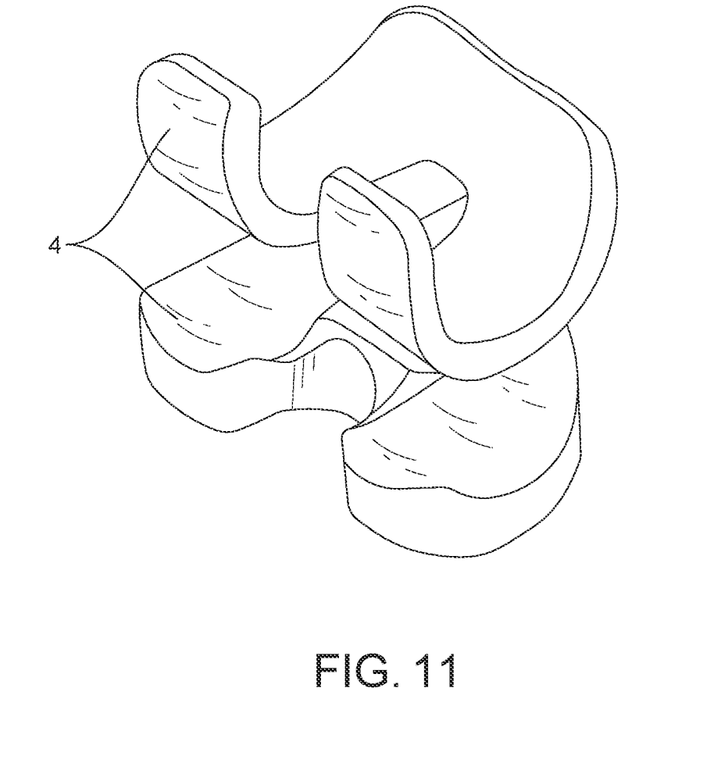

In this case, the second component 4 could be applied on the first surface 30a and/or on the second surface 30b (see FIG. 11). If desired, this component 4 could also be applied on the edge surface 30c of the femoral component 30.

Of course, if the second component 4 is applied on the first surface 30a, it defines the joint surface which, in use, will engage by roto-translation a respective joint surface of a femoral component 20. In this case, the expression first joint surface 30a would mean that this first surface is the one underlying that of actual articulation defined by the second component 4.

If in alternative or in addition to this the second component 4 is applied on the second surface 30b, it defines the connection surface which, in use, will engage or come into contact with the femur.

In this regard, the main component 30 has holes 3 (not visible in the figures) that pass through or not.

In this regard, the holes 3 could either extend from the first 30a to the second surface 30b or be blind holes on one or both of these faces.

Preferably, in this case the holes 3 could be formed in a substantially uniform manner and as indicated above on the first surface 30a.

Clearly, a femoral component could be in one piece or even include several elements suitably constrained to each other, for example with bone cement.

Also in the case of a main component of a tibial 20 or femoral 30 component, reference elements 7 could be provided to define the area of application of the dough on a respective surface 20a, 20b, 30a, 30b, which in this case could have a portion of concave or recessed application, therefore with a raised edge. These reference elements may comprise pegs or projections 7 which extend spaced from each other by a surface of the main component 20, 30. For the description of the pegs or projections, the foregoing applies.

Figure 8:
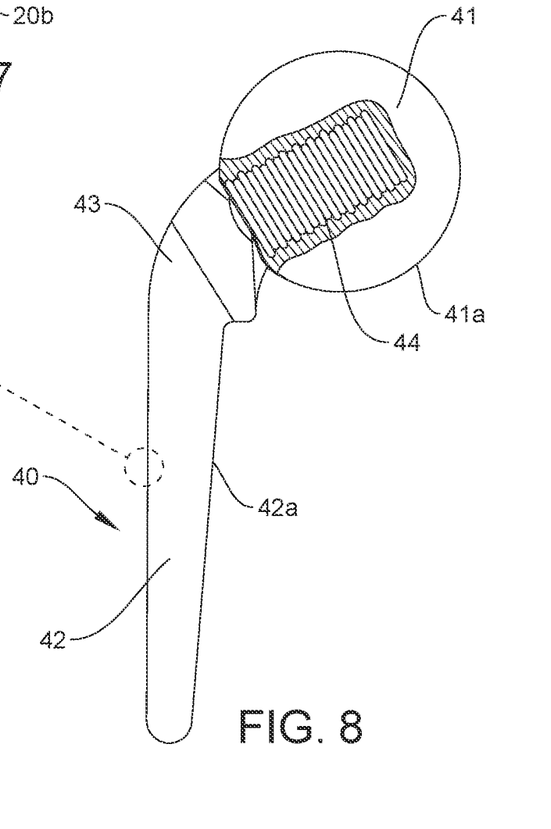

As indicated above, a device according to the present invention could also be a temporary and disposable spacer device for the hip or shoulder joint (see FIG. 8).

The main component 40 of a hip or shoulder spacer device, according to the present invention, could include a head 41, suitable for being placed in the acetabular cavity of the hip joint or in the glenoid cavity of the shoulder joint, an rod-like element or stem 42, adapted to be constrained at the bony end of the shoulder joint, or upper humeral end, or at the bony end of the knee joint, or upper femoral end.

The head 41 or the rod-shaped element or stem 42 could be made in one piece or in separate pieces suitably connected by means of screw connection means or interlocking connection means or other connection means.

In this case, the main component 40 of such a spacer also includes an intermediate component 43 that acts as a fitting or connecting or continuity element between the head 41 and the rod-like element and can have a substantially "elbow" or L-shape. or with another suitable shape.

This intermediate component 43 can be in one piece with the head 41 or the rod-shaped element 42 or only with the latter or a piece separate from both 41 and 42 and connected to them by means of suitable connection means, for example screw 44.

In this case, the second component 4 (not shown in FIG. 8) could be applied on the external surface 41a of the head 41 and/or on the external surface 42a of the rod-like element 42. If desired, this component 4 could also be applied on the external surface of the intermediate component 43.

Figure 8A:
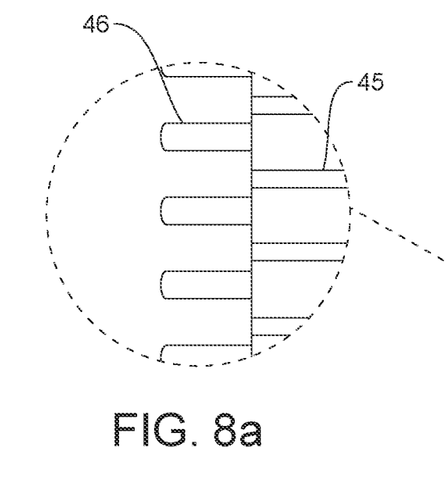
FIG. 8a shows a detail view of FIG. 8.
Figure 9A:
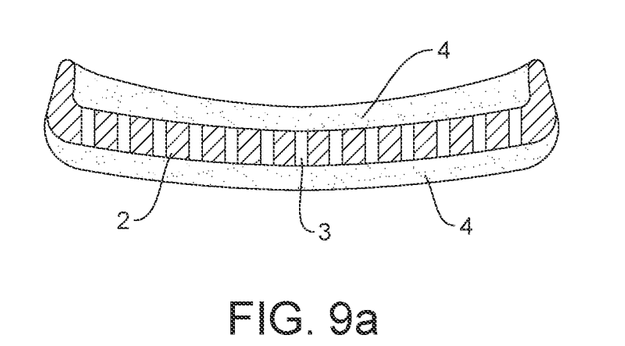
FIGS. 9a and 9b show two different embodiments of the invention, in which the second component is applied to opposing surfaces of the main support component (FIG. 9a), and in which the second component completely envelopes the main support component (FIG. 9b).
Figure 9B:
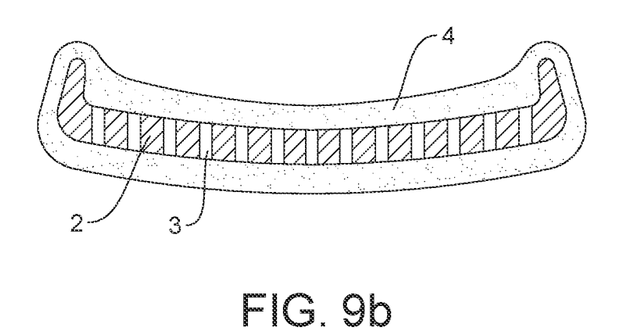

In this regard, the head 41 and/or the rod-like element 42 has blind or through holes. FIGS. 8 and 8a depict an embodiment, in which the rod-like element 42 has through holes 45 and pegs or projections 46.

With regard to this, the holes 3 could be extended transversely through the head 41 and/or the rod-shaped element 42.

As regards the materials for obtaining the main component 20, 30 or 40 and the second component 4, as well as the dimensions of the latter and of the holes, the same applies as previously described.

Even in the case of a main component of a tibial component 40, reference elements 7 could be provided for defining the area of application of the dough on a respective surface 41a, 42a, which in this case could have a concave or recessed portion of application, therefore with a raised edge. These reference elements may comprise pegs or projections 7 which extend spaced from each other from a surface of the main component 40. For the description of the pegs or projections, the foregoing applies.

As already indicated above, a device obtained starting from the main component 20, 30, 40 does not include any closure component, but it consists only of the main support component 20, 30, 40 and the second component 4 which constitute an implantable assembly as it is, and without the need for other elements, in the human body. More specifically, no closing components are provided which define together with the main component a positioning zone of the second component.

In essence, the main component 20, 30, 40 and the second component 4 define all the external surfaces of the device 1, i.e. the surfaces of the same that will come or are destined to come into contact with respective parts of the human body, such as bones, biological fluids, skin, etc.

With regard to this aspect, the second component 4 defines one or more work surfaces, in use, external or intended to be external in use or during implantation in the human body of the device 1.

Such external work surface/surfaces 4a will therefore complete together with other surfaces 20a, 20b, 20c, 30a, 30b, 30c, 41a, 42a defined by the main component 20, 30, 40 the exterior of the device, i.e. the surfaces of the same that will come into contact with respective parts of the human body, such as bones, biological fluids, skin, etc.

In the event then that the second component 4a covers all the surfaces of the main component 20, 30, 40, it will therefore define all the surfaces of the device towards the outside of the same.

Advantageously, in this case the second component 4 is applied so as to protrude with respect to or be flush or in line and not in recess with the end of a delimiting edge of an application area of the second component 4 on a surface of a such main component 20, 30, 40.

A device 1 according to the present invention can be obtained by a method which first of all provides to provide the main support component 2, 20, 30, 40 (see FIGS. 1, 2) which can be obtained with any suitable method, for example molding, if desired three-dimensional molding and to prepare (subsequently or even before this step) a dough (see FIG. 3) including a matrix of a first compound and a pharmaceutical or medical substance dispersed in the matrix.

The main support component 2, 20, 30, 40 can advantageously be obtained by means of 3D printer with a wire or powder, if desired of polystyrene (PS), polyether ether ketone (PEEK), polyethylene (PE), polypropylene (PP) in so that the printed material does not contain antibiotic or a pharmaceutical or medical substance, because the melting of the plastic wire could demolish or degrade it.

Then, by spreading, spraying, dipping, casting, molding or in another suitable way, preferably manually (see FIG. 4) or using a special tool or machine, the dough is applied on at least a first surface 2a of the main support component 2 to then make or allow the dough 5 to harden or solidify on the main component 2.

The application or coating or spraying step can, for example, be carried out by the surgeon extemporaneously or in any case just before, if desired a few minutes, the use or implantation of the device.

Figures 1, 2:
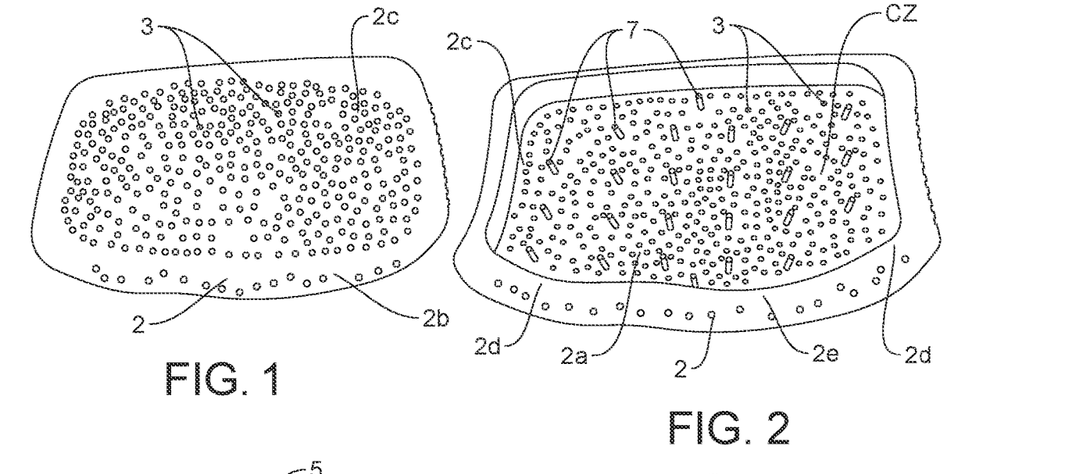
FIGS. 1 to 6 show relative steps for obtaining a device according to the present invention.
Figure 3:
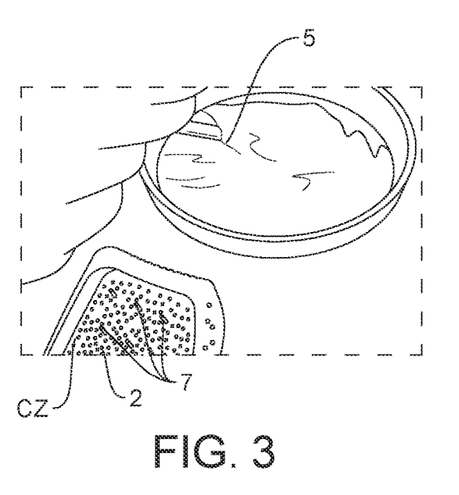
Figure 4:
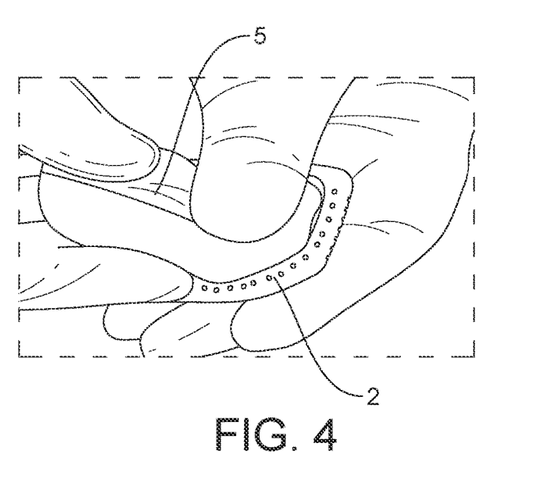
Figure 5:
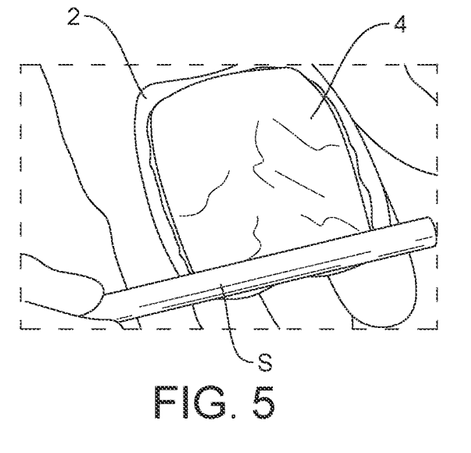
Figure 6:
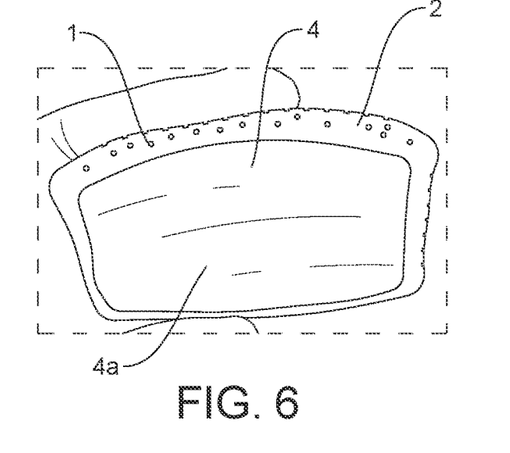

It is then possible, if necessary, to remove any dough on access, for example using a special spatula SP (see FIG. 5).

Following the hardening or solidification of the stiffening component 4 close to the main component, a much more robust or resistant device is advantageously obtained.

As will be ascertained, thanks to the present invention it is possible to first made a main support component 2, 20, 30, 40, which has essentially or for the most part the final configuration of the device, but is free of pharmaceutical or medical substances, such as an antibiotic, whereby the authorization phase from the component bodies of this main component 2, 20, 30, 40 is clearly simplified because it does not present drugs. Subsequently, just before use, the surgeon, thanks to his competence, will be able to add a stiffening dough, such as an antibiotic bone cement that will give the final product the desired characteristics of strength or mechanical resistance, if the second component is for stiffening, and/or pharmacological efficacy, if in particular the second component 4 is a component intended to convey, in use, the pharmaceutical or medical substance from the device 1 towards the outside of the same and at the implantation site.

In this way it is possible to obtain custom or tailor/customizable products for each individual patient, for example in plastic or metal materials, for example by laser sintering of metal powder, even with the creation of complex structures that cannot be obtained by an injection molding press.

Thanks to this invention, it is possible to make components for retention of at least one pharmaceutical or medical substance to be released outside them and subsequent spacers for any region of the human body, or even prosthesis for the skull or rib prosthesis, for example following detections by CAT.

This containment component can be solid bodies configured substantially as a hip or shoulder spacer or wall or plate as in the case of cranial prostheses and knee spacers.

As an alternative to the method indicated above, a main component for a device according to the present invention could also be obtained with a sintering process.

The latter, in short, includes an initial step of forming a product from a powdered material or a mixture of powdered materials that, initially, are pressed and formed inside a mold.

Subsequently, the pressed component thus formed, also known as green component, is subject to the sintering step by which the individual granules are at least partially melted together, thus resulting in a compact finished product.

The powder material to be sintered is generally mixed with solvents or adhesives or binders which favor the initial forming step (generating a partial gluing of the powders), which are subsequently dispersed during the subsequent process steps.

By way of example, the powder material can have a particle size of between 1 and 1000 microns.

The sintering step usually takes place at high temperature, by means of dry heat or by steam, leading to one at least partial surface thermal melting. High pressure, solvent or binder and heat can also be used simultaneously.

Such powder material can include, for example, materials such as thermoplastic or thermosetting plastics, metals, ceramics, composite materials, and in general materials that are biocompatible and implantable in the human body, without therefore causing a rejection by the tissues they are in contact with.

The powdered material can belong to other types of materials than those indicated above, provided that it is biocompatible and implantable in the human body without any limitation.

By means of the aforementioned sintering process it is possible to obtain a compact or porous main component delimiting a plurality of holes with the meaning indicated above.

According to a further version, the main component can be made by means of an injection molding process, for example in a press, of a thermoplastic resin, of the biocompatible type and implantable in the human body.

As indicated above, furthermore the main component 2 can be produced with an additive process such as, for example, a three-dimensional printing process of a biocompatible and implantable material in the human body, of the type previously described or preferably of an acrylic nature.

Through the three-dimensional printing process, it is possible to obtain a main component of a porous type or having a honeycomb structure and therefore substantially trabecular.

According to a version of the present invention, in the three-dimensional printing process, for example, the use of wire materials made of thermoplastic resins such as PMMA, PE, PP, PEEK etc. can be envisaged.

However, it is possible to use materials other than those described above, provided they are biocompatible and implantable in the human body, without thereby departing from the scope of protection of the present invention.

Once realized, the main component 2 can be covered in whole or in part with a second component, which, by solidifying or hardening, determines the creation of a spacer device or device to be implanted, which has become one with the main component.

In this way it is possible to obtain custom or personalized/customizable products for each individual patient.

Thus, for example, it is possible to create a main component to be equipped with at least one pharmaceutical or medical substance to be released outside, and subsequent spacers for any region of the human body, or even prostheses for the skull or rib prostheses (for example from CAT data).

The main component must correspond to the external geometry of the spacer to be made, since the external portion of this spacer device—and therefore its conformation and dimensions correspond to those of the containing and/or closing body that determine its portion and the external surface.

Preferably, the aforementioned first liquid or fluid compound can be used in a spacer device in which the main component does not have a high mechanical resistance, but is provided with the same by means of the second stiffening component.

The first compound can be a hardening or solidifiable liquid or fluid. As indicated above, the filling material can be bone cement.

According to one version, the filling material is prepared by the surgeon, who adds at least one pharmaceutical or medical substance to the components of the filling material.

It will also be understood how the spacer device could comprise also a reinforcement core for the spacer device itself, if desired a metal core embedded in the main component.

The invention thus conceived is susceptible of numerous modifications and variations, all of which are within the scope of the inventive concept.

The features presented for one version or embodiment can be combined with the characteristics of another version or embodiment, without departing from the scope of protection of the present invention.

Furthermore, all the details can be replaced by other technically equivalent elements. In practice, the materials used, as well as the contingent shapes and dimensions, may be any according to requirements without thereby going out the scope of the protection of the following claims.

The invention claimed is:

1. An implantable device in a human body consisting of:
a first component or main support component delimiting a plurality of through holes; and
a second component applied on at least one outer surface of the main support component,
the second component comprising a dough applied and hardened or solidified on the at least one outer surface and at least in part within the holes,
the dough including a matrix of at least one first compound and at least one pharmaceutical or medical substance dispersed in the matrix,
the second component being a component that stiffens or increases a resistance of the main component, and/or a component adapted to convey, in use, the at least one pharmaceutical or medical substance from the implantable device to an outside thereof and into an implant site,
wherein the main support component comprises a plurality of reference elements that define an application area of the dough on the at least one outer surface,
wherein the reference elements comprise pegs extending, spaced from each other, from the at least one outer surface, the dough entirely covering the pegs and extending therebetween,
wherein the implantable device comprises no closing component,
wherein the main support component and the second component constitute an assembly implantable in the human body,
wherein the pegs are distributed on the at least one outer surface, so that an area defined by a perimeter or line passing through the outermost periphery of the plurality of reference elements is at least 60% of the at least one outer surface,
wherein the main support component includes a raised perimeter or delimitation edge of an application area of the second component on the at least one outer surface of the main support component, and
wherein the second component is applied so as to be flush or in line with, and not recessed within, an end of the raised perimeter or delimitation edge, and to fill all spaces between the pegs.

2. The implantable device according to claim 1, wherein the holes have a passage section between 0.05 and 10 mm.

3. The implantable device according to claim 2, wherein the holes are at a distance from each other of 0.1 to 5 mm.

4. The implantable device according to claim 1, wherein the main support component has a thickness of 0.1 to 100 mm.

5. The implantable device according to claim 1, wherein the second component has a thickness of 0.1 mm to 100 mm.

6. The implantable device according to claim 1, wherein the main component and the second component define all outer surfaces of the implantable device, the outer surfaces being adapted to come into contact with respective parts of the human body.

7. The implantable device according to claim 1, wherein the at least one outer surface delimits a concave area configured to house the second component.

8. The implantable device according to claim 7, wherein the concave area has a height of 5 to 200 mm.

9. The implantable device according to claim 1, wherein the implantable device is configured as a joint spacer, a prosthesis, or a component of a joint spacer or of a prosthesis.

10. The implantable device according to claim 9, wherein the main support component has substantially a same final shape as the implantable device, with a concave area and/or a convex surface enveloped, in whole or in part, within the second component.

11. The implantable device according to claim 1, wherein the main component is made of a biologically compatible material.

12. The implantable device according to claim 1, wherein the first compound is selected from the group consisting of bone cement, inorganic hydraulic cement, and ceramic cement.

13. The implantable device according to claim 1, wherein the pharmaceutical or medical substance comprises at least one antibiotic.

14. An implantable device in a human body consisting of:
a first component or main support component delimiting a plurality of through holes; and
a second component applied on at least one outer surface of the main support component,
the second component comprising a dough applied and hardened or solidified on the at least one outer surface and at least in part within the holes,
the dough including a matrix of at least one first compound and at least one pharmaceutical or medical substance dispersed in the matrix,
the second component being a component that stiffens or increases a resistance of the main component, and/or a component adapted to convey, in use, the at least one pharmaceutical or medical substance from the implantable device to an outside thereof and into an implant site,
wherein the main support component comprises a plurality of reference elements that define an application area of the dough on the at least one outer surface, wherein the reference elements comprise pegs extending, spaced from each other, from the at least one outer surface, the dough covering the pegs and extending therebetween, wherein the implantable device comprises no closing component, wherein the main support component and the second component constitute an assembly implantable in the human body, wherein the pegs are distributed on the at least one outer surface, so that an area defined by a perimeter or line passing through the outermost periphery of the plurality of reference elements is at least 60% of the at least one outer surface, and wherein the main support component includes at least two opposing outer surfaces, and wherein the second component is applied on both of the at least two opposing outer surfaces.

15. The implantable device according to claim 14, wherein the second component completely envelopes the main support component.

16. A method of obtaining a device implantable in a human body, comprising a first component or main support component delimiting a plurality of through holes and a second component applied on at least one outer surface of the main support component, the second component comprising a dough applied and hardened or solidified on the at least one outer surface and at least in part within the holes, the dough including a matrix comprising a first compound and a pharmaceutical or medical substance dispersed in the matrix, the second component being a component that stiffens or increase a resistance of the main support component and/or a component adapted to convey, in use, the pharmaceutical or medical substance from the device to an outside thereof and in an implant site, wherein the main support component comprises a plurality of reference elements that define an application area of the dough on the at least one outer surface, wherein the reference elements comprise pegs extending, spaced from each other, from the at least one outer surface, the first component having a raised perimeter or delimitation edge of an application area of the second component on the at least one outer surface of the main component, the method comprising the steps of:

providing the main support component;

preparing the dough including the matrix of the first compound and the pharmaceutical or medical substance dispersed in the matrix;

applying the dough on at least one outer surface of the main support component before implanting the device in the human body to entirely cover the pegs and extend and fill all spaces therebetween; and causing to, or letting, the dough harden or solidify.

* * * * *